US00PP21380P3

(12) United States Plant Patent
Vinson et al.

(10) Patent No.: US PP21,380 P3
(45) Date of Patent: Oct. 12, 2010

(54) STRAWBERRY PLANT NAMED 'SWEET EVE'

(50) Latin Name: ***Fragaria×ananassa* Duch.**
Varietal Denomination: Sweet Eve

(75) Inventors: Peter Edward Vinson, Hernhill Faversham Kent (GB); Simon Peter Warren, Hernhill Faversham Kent (GB)

(73) Assignee: Edward Vinson Limited, Kent (GB)

( * ) Notice: Subject to any disclaimer, the term of this patent is extended or adjusted under 35 U.S.C. 154(b) by 0 days.

(21) Appl. No.: 12/320,146

(22) Filed: Jan. 21, 2009

(65) Prior Publication Data

US 2009/0229025 P1 Sep. 10, 2009

(30) Foreign Application Priority Data

Feb. 18, 2008 (QZ) ..... PBR 2008/0368

(51) Int. Cl.
*A01H 5/00* (2006.01)

(52) U.S. Cl. ..... Plt./209

(58) Field of Classification Search ..... Plt./209, Plt./208

See application file for complete search history.

*Primary Examiner*—Kent L Bell
(74) *Attorney, Agent, or Firm*—Rosenberg, Klein & Lee

(57) ABSTRACT

This invention relates to a new and distinctive day-neutral cultivar, designated as 'Sweet Eve', primarily adapted to the growing conditions in the United Kingdom. This day-neutral (everbearing) cultivar is primarily characterized by an upright growth habit, a medium to large fruit size having superior uniformity, berries exhibiting a glossy bright orange-red appearance, significantly better flavored, aromatic berries, significantly firmer fruit skin, increased numbers of flower trusses and fruit trusses per plant, very moderate petiole pubescence, and an early to mid season production with substantial yields.

16 Drawing Sheets

Figure 1:
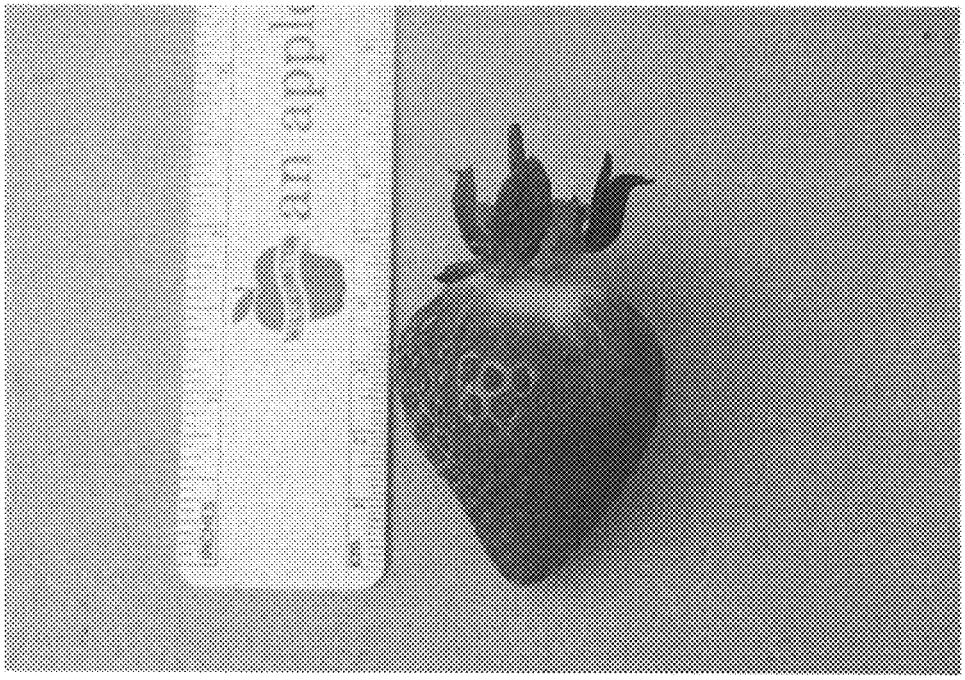

Genus and species: *Fragaria ×ananassa* Duch.
Cultivar denomination: 'Sweet Eve'.

BACKGROUND OF THE INVENTION

The new and distinct cultivar of strawberry originated from a controlled cross performed in a glasshouse as part of an ongoing breeding program in Kent, United Kingdom between the agricultural selections '01BB64' (not patented) and 'S01R5' (not patented) in 2003.

SUMMARY OF THE INVENTION

The present invention relates to a new and distinct day-neutral (everbearing) strawberry cultivar designated as 'Sweet Eve'. The cultivar is botanically known as *Fragaria ×ananassa* Duch. Under growing conditions in the United Kingdom this day-neutral (everbearing) cultivar has shown significant improvements over the variety 'Albion' (U.S. Plant Pat. No. 16,228). Improvements include, but are not limited to, improved fruit quality, significantly greater Brix levels, superior eating quality, aroma, skin firmness, enhanced shelf life, and paler fruit color.

The female parent, '01BB64', is a day-neutral cultivar cropping in the United Kingdom in July August, and September. '01BB64' exhibits a moderate crop that is below standards generally accepted for commercialization. Additionally, the shape and size of '01BB64' fruit is highly variable and also below standards generally accepted for commercialization. '01BB64' does, however, express fruit having exceptional flavor and high fragrance. The fruit firmness of '01BB64' is extremely soft and the fruit is pale in color. '01BB64' was selected as a parent for the flavor characteristics expressed. There are no other characteristics which would render '01BB64' commercially viable.

The male parent, 'S01R5', is a Mediterranean short day cultivar that was selected in Spain. 'S01R5' crops from March until the end of May when grown in Spain. 'S01R5' was selected as a parent because the cultivar expresses an extraordinary combination of firmness and flavor. 'S01R5' exhibits fruit firmness greater than that found in typical commercialized strawberry varieties while additionally expressing high sugars, high aroma and exceptional flavor. Despite the exceptional eating qualities of the fruit of this cultivar, 'S01R5' has a fruit size below standards generally accepted for commercialization. Furthermore, 'S01R5' fruit has an appearance below commercial expectation. Specifically, 'S01R5' fruit is pointed, ridged, and dark in color. 'S01R5' does generate a good yield as it relates to fruit number, however, the small fruit size and the high number of culls make the marketable yield of this cultivar low when considered for commercialization purposes.

The female parent, '01BB64', is a hybrid of *Fragaria ×ananassa* Duch and the male parent, 'S01R5', was derived from an open pollinated seed of an unknown cultivar of *Fragaria ×ananassa* Duch. The female parental cultivar, '01BB64', was selected in 2001 in a breeding field located in Kent, United Kingdom. The male parental cultivar, 'S01R5', was selected in 2001 in a breeding field located in Cartaya, Spain. Accordingly, the cultivar 'Sweet Eve' is of the species *Fragaria ×ananassa* Duch.

The seedling fruited in the summer of 2004 at the seedling field located in Kent, United Kingdom was originally designated '04AA22', and subsequently named 'Sweet Eve' for introduction. '04AA22' was selected because the cultivar produced a high yield of extremely high quality and good sized fruit. Additionally, the cultivar exhibited a firmness, shape, and flavor of outstanding quality.

'Sweet Eve' was trialed in trial plots in Kent, United Kingdom during the years 2005, 2006, 2007 and 2008. During the period of trials 'Sweet Eve' was reproduced asexually for four (4) successive years. For each trial year, asexual propagation of 'Sweet Eve' was by means of stolons (runners) and took place at the glasshouse facility as part located in Kent, United Kingdom. Additionally, during the year 2007, however, a limited number of 'Sweet Eve' plants were reproduced asexually by stolons at a propagation facility in Kent, United Kingdom. In all four (4) generations, plants were observed for trueness to type during the fruiting phase with no abnormalities being observed. Further propagation, at nurseries located at Faversham and Deal in Kent and Southampton in Hampshire, United Kingdom, was completed on a larger scale in 2008 using tissue culture plants as mother plants. This propagation demonstrated no obvious abnormalities in these plants. All propagules of 'Sweet Eve' have been observed to be true to type in that during all asexual multiplication, the vegetative and fruit characteristics of the original plant have been maintained.

The new cultivar is primarily adapted to the climate and growing conditions of south eastern England and other regions of similar climate and day length. These regions provide the necessary winter temperatures required for it to produce a strong vigorous plant and to produce fruit in the summer harvest season from June through September, depending on location.

The following list of traits, in combination, defines the new cultivar as a unique cultivar distinguishable from other commercial varieties in the region:

- upright and dense growth habit;
- medium to large fruit size having superior uniformity;
- berries exhibiting a glossy bright orange-red appearance;
- significantly better flavored berries with very strong aroma;
- significantly firmer fruit skin and flesh;
- increased numbers of flower trusses and fruit trusses per plant increase total yield per plant;
- very moderate petiole pubescence; and
- mid season production with substantial yields.

BRIEF DESCRIPTION OF THE PHOTOGRAPHS

The accompanying color photographs show typical specimens of the new cultivar, designated at various stages of development as nearly true as is possible to make in color reproductions. The depicted plant and plant parts were from the 2008 harvest season, approximately five (5) months after planting.

FIG. 1 Typical fully developed primary fruit, measured in length (cm).

Figure 2:
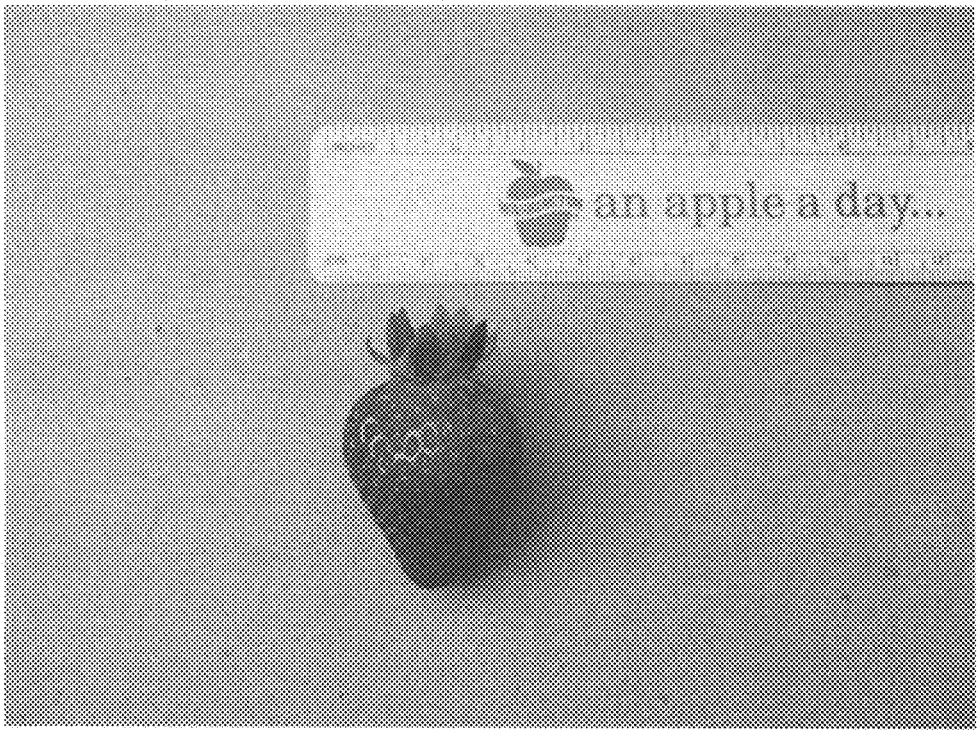

FIG. 2 Typical fully developed primary fruit, measured in width (cm).

Figure 3:
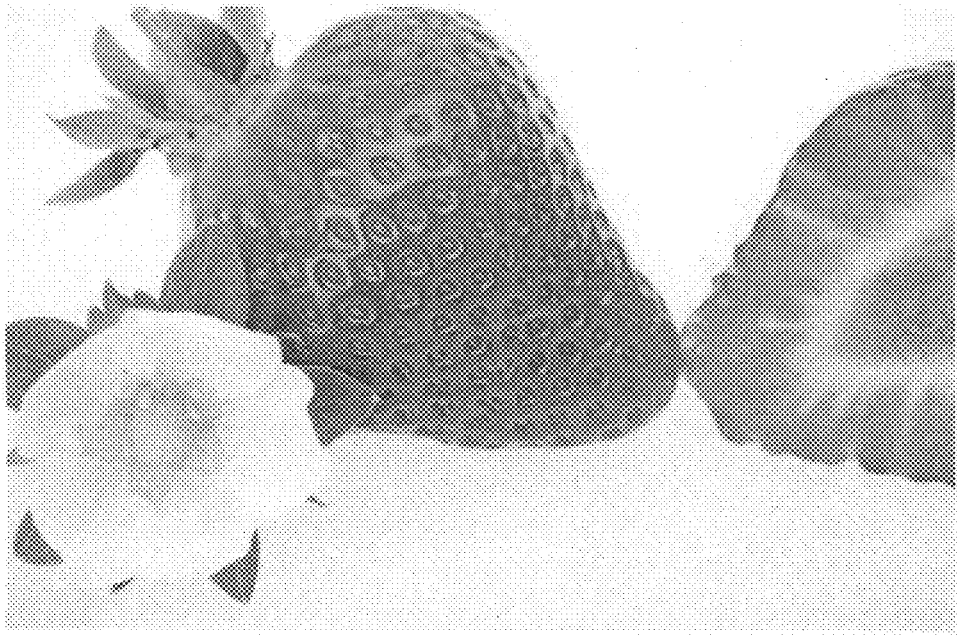

FIG. 3 Typical primary fruit and typical primary flowers.

Figure 4:
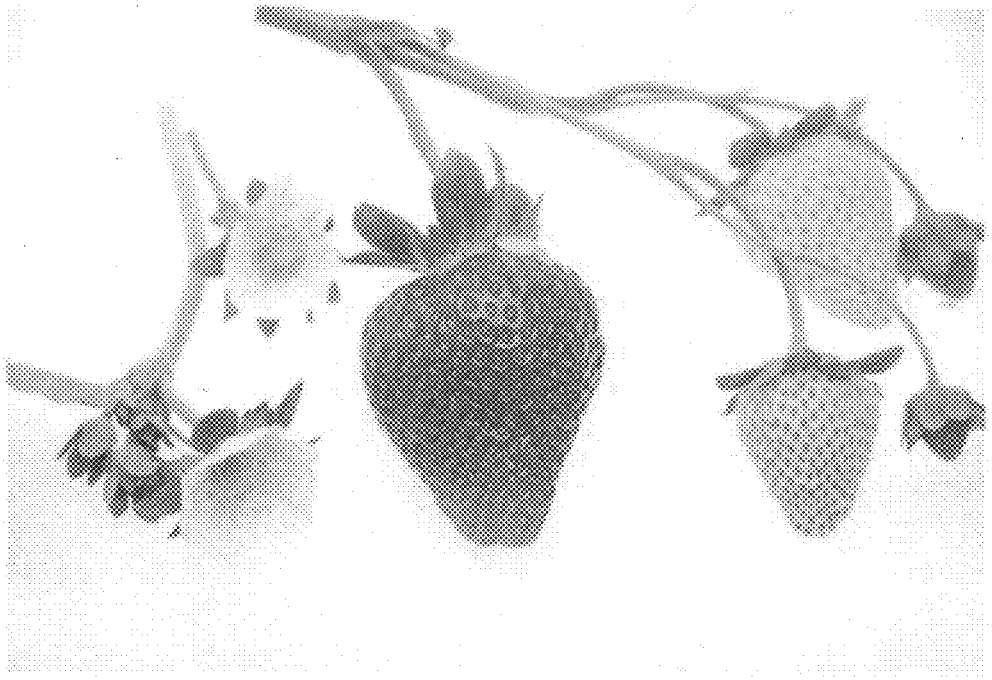

FIG. 4 Typical fruiting truss.

Figure 5:
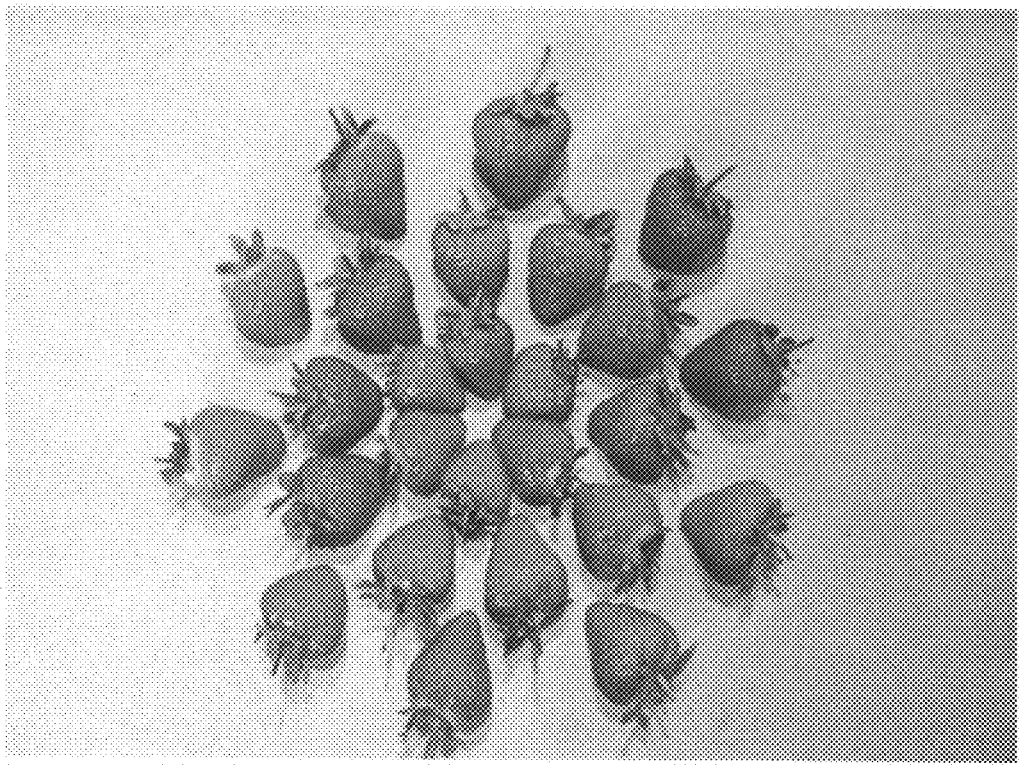

FIG. 5 A selection of large primary fruits (outer circle) having a long conical shape, secondary fruits (middle circle) having a conical shape, and tertiary fruits (inner circle) having a rounded conical shape.

Figure 6:
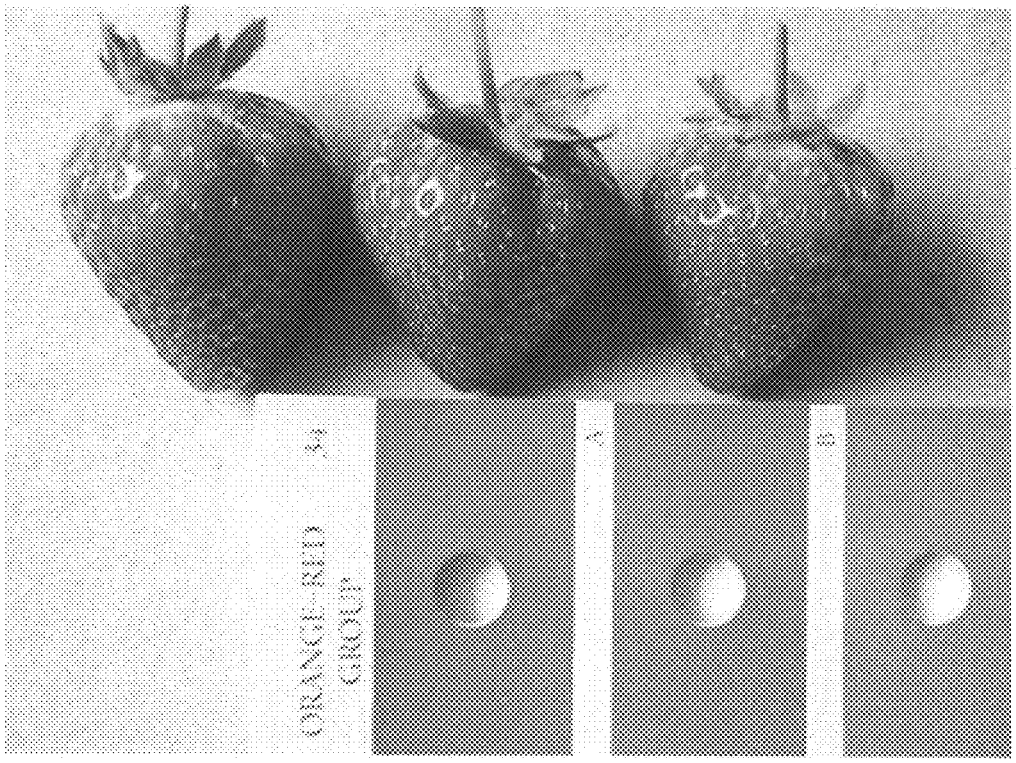

FIG. 6 'Sweet Eve' fruit skin color identified using the Royal Horticultural Society Colour Chart (34 A).

Figure 7:
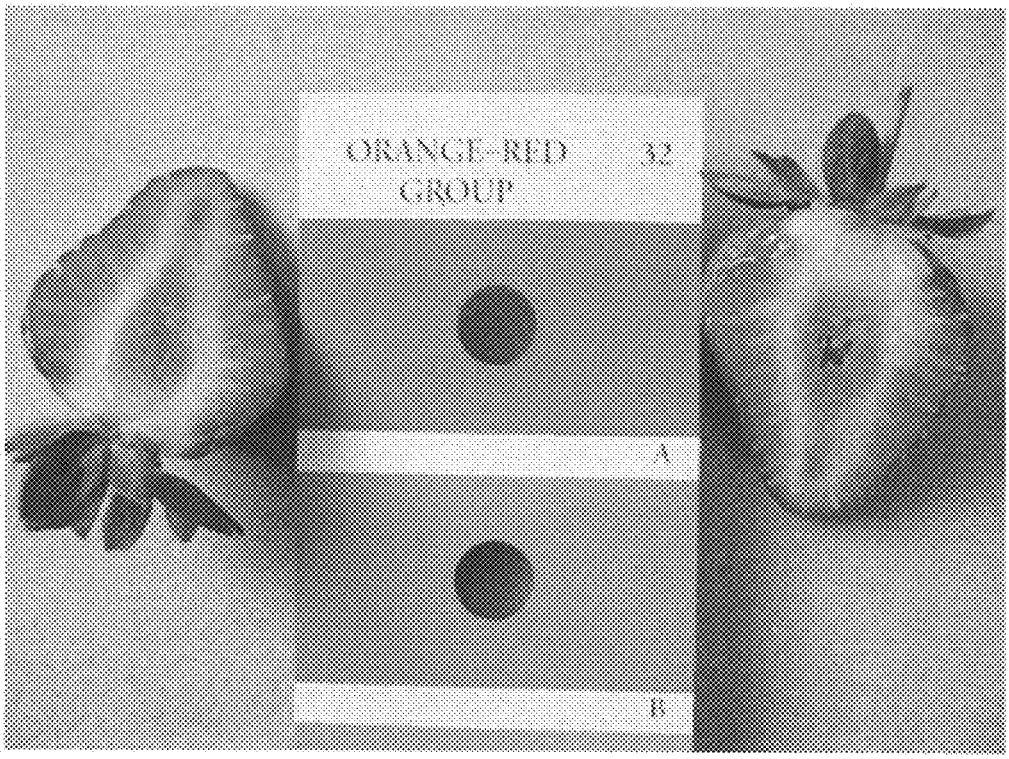

FIG. 7 Typical 'Sweet Eve' fruit interior flesh coloration near the outside fruit surface identified using The Royal Horticultural Society Colour Chart (32 A).

Figure 8:
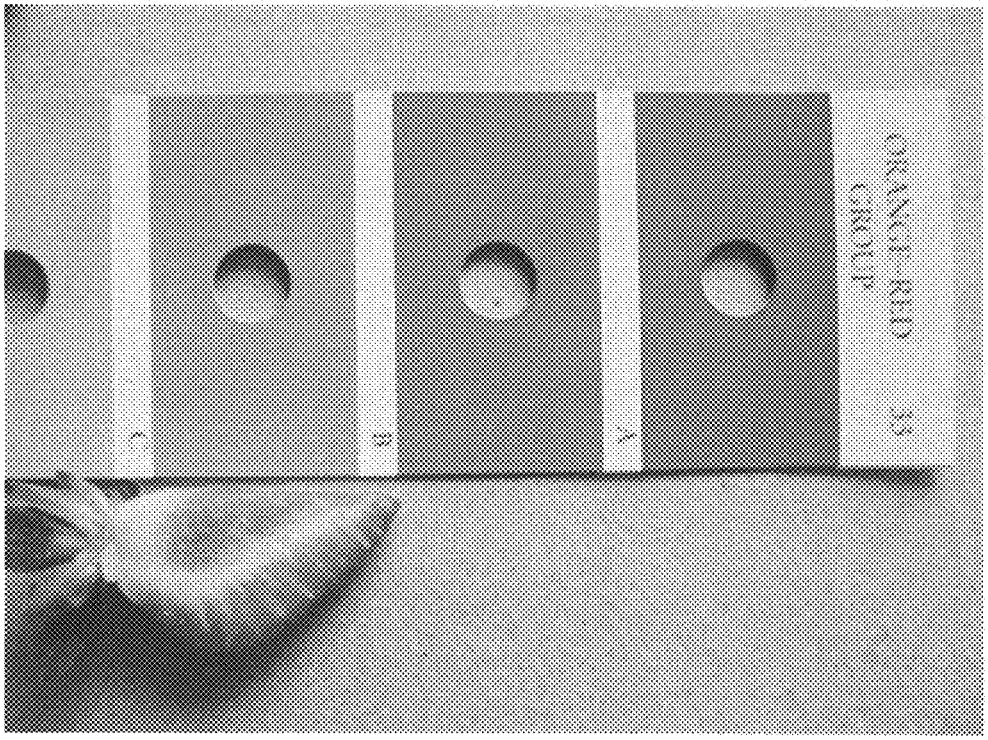

FIG. 8 Typical 'Sweet Eve' fruit inner core coloration identified using The Royal Horticultural Society Colour Chart (33 C).

Figure 9:
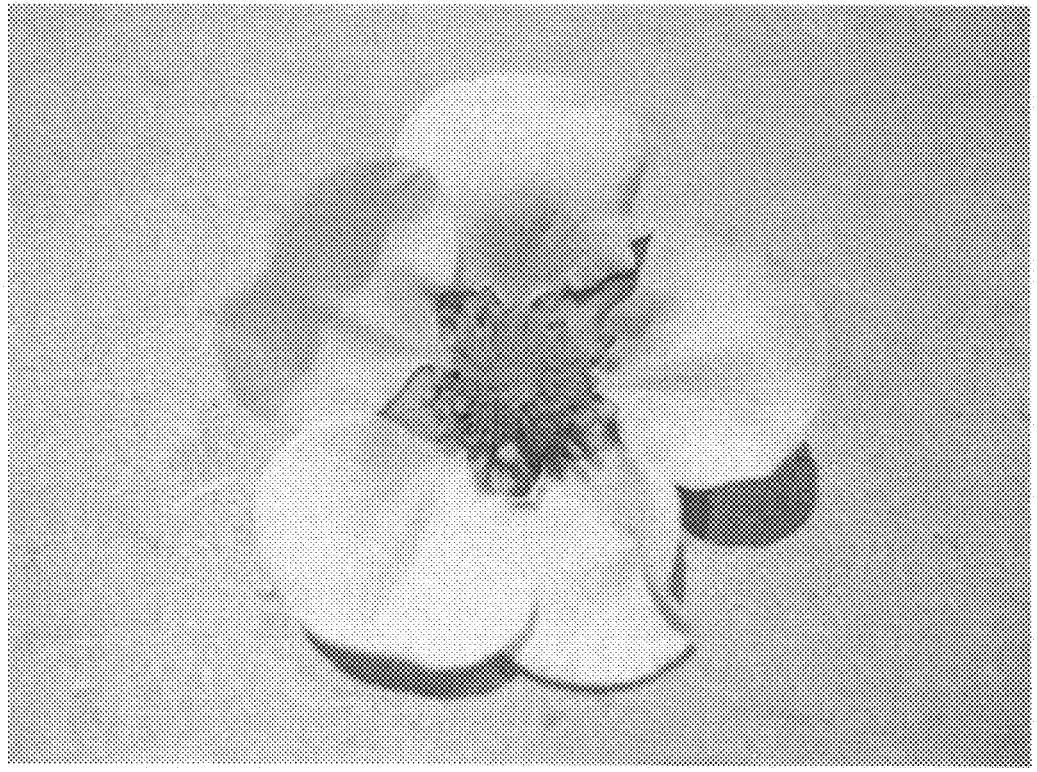

FIG. 9 A 'Sweet Eve' flower with visible corolla (petals, stamens, and ovary).

Figure 10:
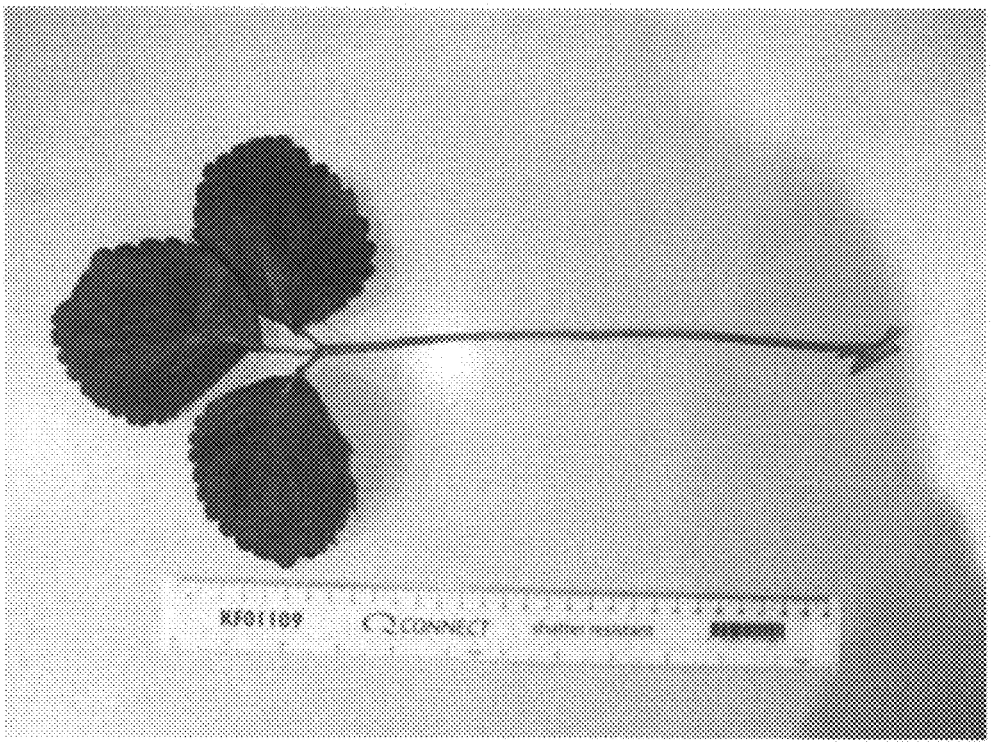

FIG. 10 A typical mature leaf with attached petiole and leafy stipule at the base of the petiole, measured in length and having slightly pointed to slightly rounded serrations and channel-like venations.

Figure 11:
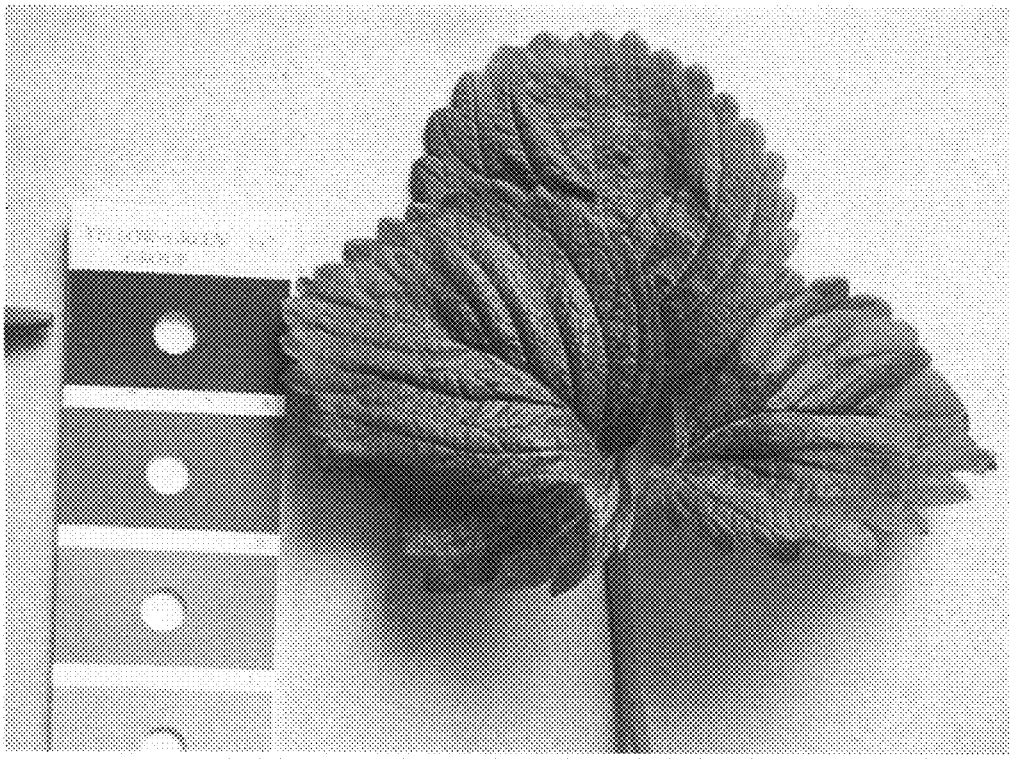

FIG. 11 Upper leaf surface color identification of a fully expanded 'Sweet Eve' leaf using The Royal Horticultural Society Colour Chart (147 A).

Figure 12:
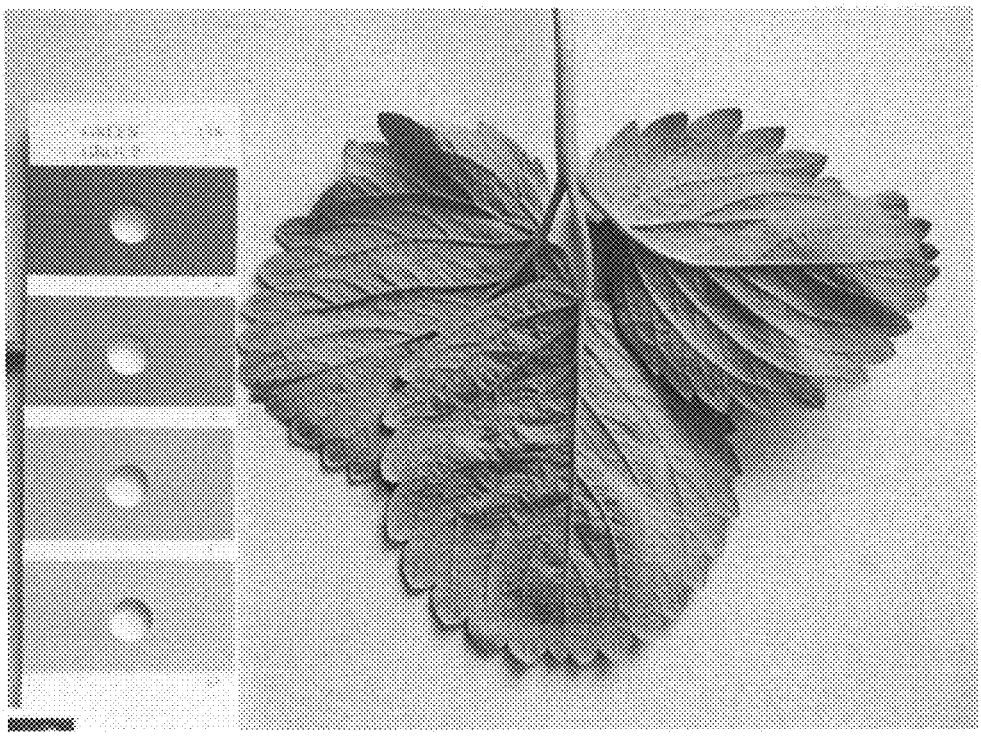

FIG. 12 Lower leaf surface color identification of a fully expanded 'Sweet Eve' leaf using The Royal Horticultural Society Colour Chart (138 B).

Figure 13:
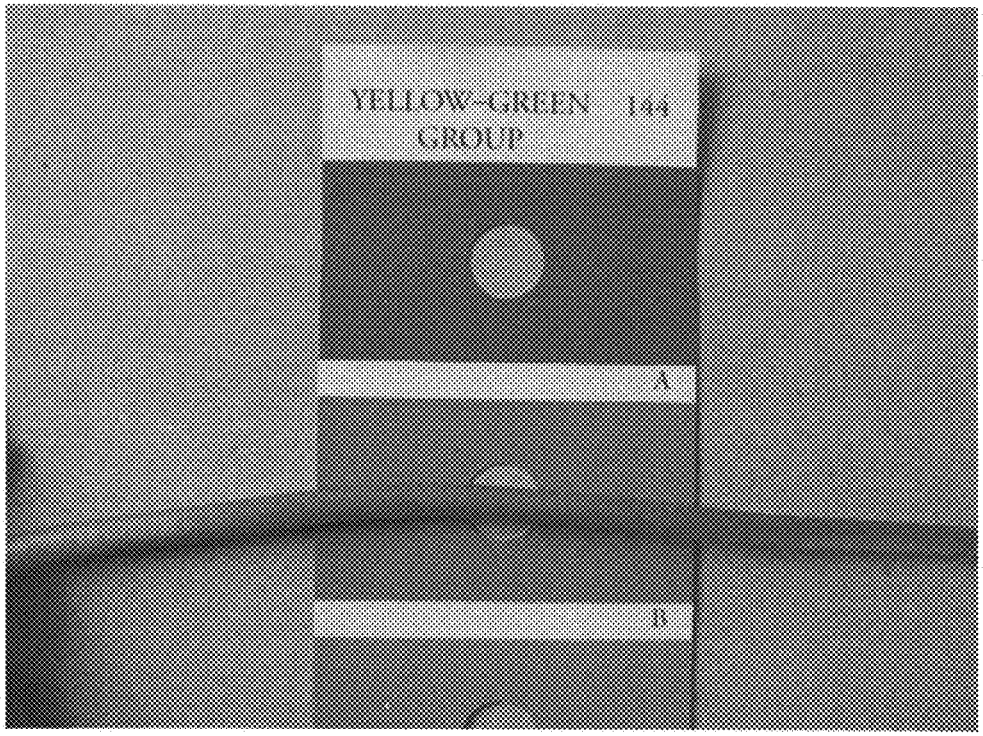

FIG. 13 Petiole color identification using The Royal Horticultural Society Colour Chart (144 B).

Figure 14:
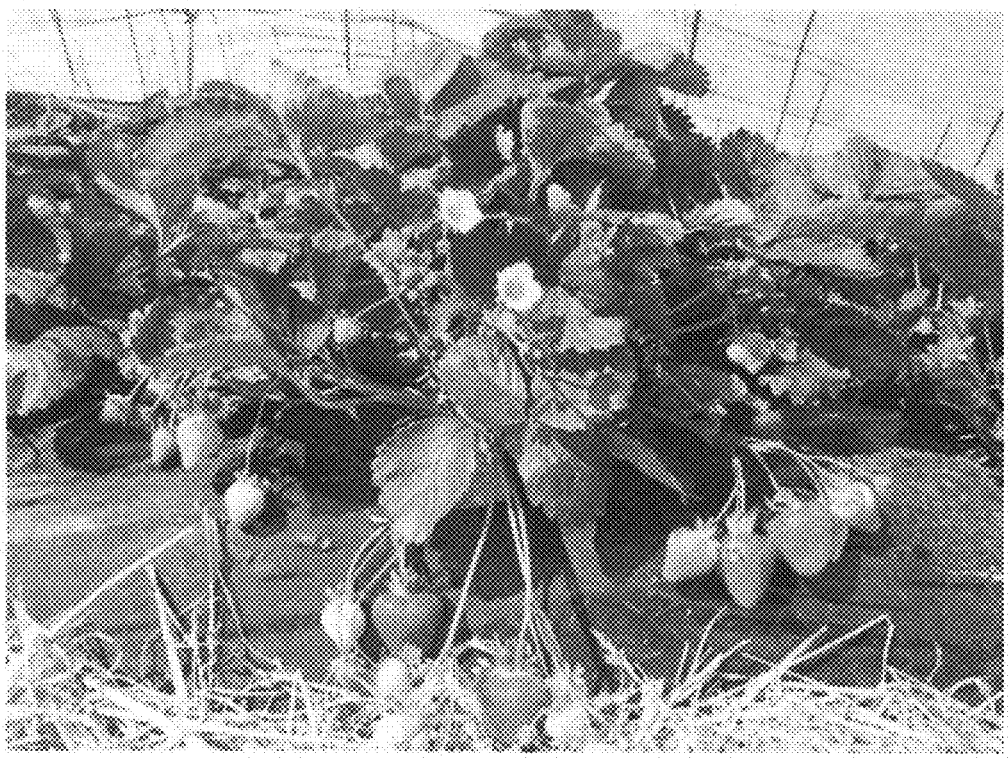

FIG. 14 Photo of a cropping 'Sweet Eve' plant in midsummer showing the typical upwards curving leaflets, with leaves, flowers, and fruits visible at various developmental stages.

Figure 15:
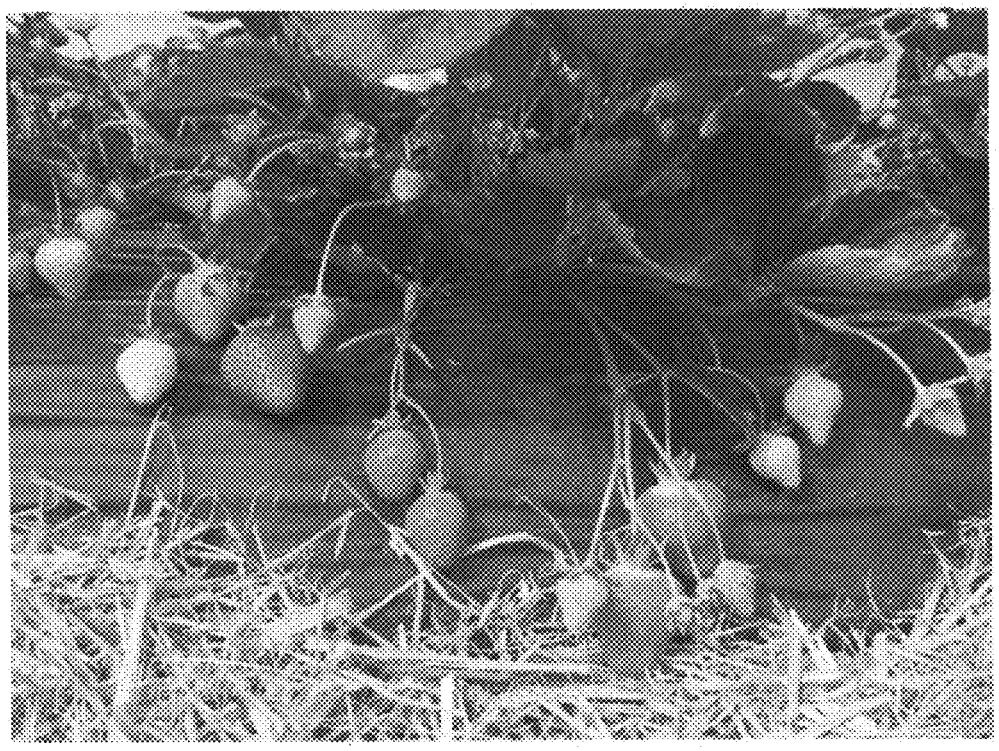

FIG. 15 Photo of a cropping 'Sweet Eve' plant in late summer showing the typical upwards curving leaflets, with leaves, flowers, and fruits visible at various developmental stages.

Figure 16:
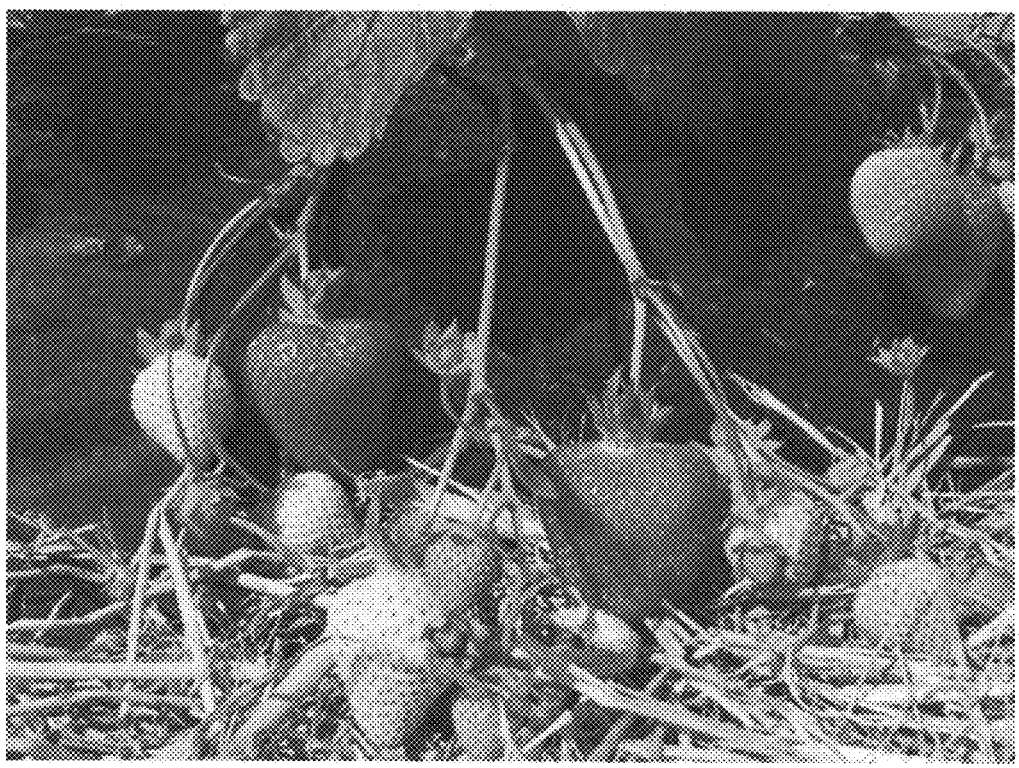

FIG. 16 Close shot of a typical mature 'Sweet Eve' primary fruit with fruits of different developmental stages are visible in the background.

DETAILED BOTANICAL DESCRIPTION OF NEW CULTIVAR

The following description of 'Sweet Eve', unless otherwise noted, is based on observations taken of plants and fruits grown in a trials field covered with tunnels and polyethylene covers as part of an ongoing breeding program in Kent, United Kingdom.

The following description is in accordance with UPOV terminology and the color terminology used herein is in accordance with The Royal Horticultural Society Colour Chart. The color descriptions and other phenotypical descriptions may deviate from the stated values and descriptions depending upon variation in environmental, seasonal, climatic, and cultural conditions.

Propagation

The new variety is principally propagated by way of stolons. Although propagation by stolons is presently preferred, other known methods of propagating strawberry plants may be used. Strawberry plants root well following transplanting.

Comparative Fruit Characteristics

The fruit characteristics of 'Sweet Eve' include, but are not limited to, the characteristics of the fruit itself, the fruit production, and the fruit quality. Fruit characteristics for 'Sweet Eve' were observed over four (4) seasons and the data was taken from the 2008 harvest season.

Table 1 shows the average fruit yield and size of 'Sweet Eve' from measurements taken during the year 2008 when subjected to the environmental and growing conditions as they existed in the United Kingdom at that time. The measurements of 'Albion' were taken in the United States and cannot reflect the average total yields or primary berry weights of 'Albion' as they might exist under the same environmental or growing conditions that 'Sweet Eve' was subjected to when grown in the United Kingdom.

In 2008 fruit harvest started on 16 June and continued through September. The plants of 'Sweet Eve' were grown in a nursery in Kent, United Kingdom and planted in March 2008.

TABLE 1

Quantitative Comparison of 'Sweet Eve' and 'Albion' Fruit Yields and Weights

| Cultivar (Average total yield in grams per plant) | Average | Cultivar (Primary berry weight in grams) | Average |
|---|---|---|---|
| 'Sweet Eve' | 1,572 | 'Sweet Eve' | 28.0 |
| 'Albion' | 2,417 | 'Albion' | 33.0 |

Table 2 compares the fruit characteristics of 'Sweet Eve' berries with another standard variety. Measurements provided were taken from fully mature (ripe) primary fruits. Fruit width is measured across the widest part of the berry, typically, across the shoulders of the berry.

TABLE 2

Quantitative Comparison of 'Sweet Eve' and 'Albion' Fruit Characteristics

| Characteristic | 'Sweet Eve' | 'Albion' |
|---|---|---|
| Exterior Color | Orange-Red 34A (RHS) | 5R 3/7 (Munsell) |
| Internal Color (Inner Core) | Orange-Red 32A (RHS) | 7.5R 4/11 (Munsell) |
| Achene Color | Yellow 3A (RHS) | 7.5R 3/6 (Munsell) |
| Mature Fruit Length Mean (mm) | 44.2 | 60.6 |
| Mature Fruit Width Mean (mm) | 38 | 49.7 |
| Mature Fruit Length/Width Ratio | 1.16 | 1.2 |
| Achenes per Primary Berry | 381.43/primary berry | 440.8/primary berry |
| Achene Position | Even to indented | Mostly indented, some even |

Table 3 compares the fruit quality characteristics of 'Sweet Eve' with the fruit quality characteristics of 'Albion.' Comparisons of fruit quality include, but are not limited to, flesh firmness, soluble solids (as measured by % Brix), and acidity.

TABLE 3

Comparison of 'Sweet Eve' and 'Albion' Fruit Quality Characteristics

| Characteristic | 'Sweet Eve' | 'Albion' |
|---|---|---|
| Fruit Skin Firmness | Very firm | Firm to very firm |
| Flesh Firmness | Medium firm to firm | Firmer internal texture |
| Fruit Appearance | Bright orange-red glossy | Dark fruit, less uniformity in shape, increased ridging, and low gloss |
| Fruit Aroma | Very strong aroma | Medium aroma |
| Fruit Sweetness | High sugars, strong sweetness | Medium sweetness |
| Soluble Solids (% Brix) | 11.1% | 8.5% |
| Acidity | Very low acidity | Medium acidity |

Detailed fruit characteristics of 'Sweet Eve':

*Ratio of length to width.*—Longer than broad.

*Size.*—Medium to large.

*Predominant shape.*—Long conical shape with rounded shoulders.

*Aroma.*—Very strong.

*Differences in shape between primary and secondary fruit.*—Slight.

*Differences in shape between primary and tertiary fruit.*—Slight.

*Band without achenes.*—Narrow to medium width.

*Color of mature fruit (ripe).*—Bright orange-red (Orange-Red 34A).

*Evenness of color.*—Very even.

*Glossiness.*—Very high.

*Achene position.*—Even to slightly indented.

*Attitude of the calyx segments.*—Typically recurved.

*Color of the upper (adaxial) surface of the calyx.*—Green (Green 138A).

*Color of the lower (abaxial) surface of the calyx.*—Green (Green 141A).

*Size of calyx in relation to fruit diameter.*—Generally smaller.

*Firmness of skin.*—Very firm.

*Firmness of flesh.*—Moderate firmness.

*Color of flesh.*—Interior flesh coloration near the outside edges of the fruit surface approaches bright orange-red (Orange-Red 32A) and the inner core approaches red (Orange-Red 33C).

*Hollow center.*—Weakly expressed in primary fruit and not expressed in secondary and tertiary fruit.

*Achene color.*—Generally bright yellow (Yellow 3A), however, when fully exposed to light, achenes are orange-red (Orange-Red 33B) in color.

*Time of flowering (50% of plants at first flower).*—Medium to early.

*Time of ripening (50% of plants with first ripe fruit).*—Medium to early.

*Type of bearing.*—Day-neutral (everbearing).

Comparative Plant Characteristics

Table 4 is a comparison of the plant characteristics of 'Sweet Eve' with the plant characteristics of 'Albion' when the varieties were grown side-by side in Kent, United Kingdom. Comparisons of plant characteristics include differences in plant height, width, and breadth.

TABLE 4

Quantitative Comparison of 'Sweet Eve' and 'Albion' Plant Characteristics

| Characteristic | 'Sweet Eve' | 'Albion' |
|---|---|---|
| Plant Height Mean (mm) | 350 | 252 |
| Plant Width Mean (mm) | 430 | 388 |
| Plant Breadth Mean (mm) | 450 | 370 |

Detailed plant characteristics of 'Sweet Eve':

*Size.*—Medium to large.

*Habit.*—Upright and slightly compact with dense canopy.

Comparative Foliage Characteristics

Table 5 compares the leaf characteristics of 'Sweet Eve' with the leaf characteristics of 'Albion.' Foliage characteristics are taken from a fully mature tri-foliate leaf during mid-season.

TABLE 5

Quantitative Comparison of 'Sweet Eve' and 'Albion' Plant Foliage Characteristics

| Characteristic | 'Sweet Eve' | 'Albion' |
|---|---|---|
| Adaxial Surface Color | Yellow-Green 147A (RHS) | 5GY 3/2 (Munsell) |
| Abaxial Surface Color | Green 138B (RHS) | 5GY 5/6 (Munsell) |
| Mid-tier Leaflet Length Mean (mm) | 97 | 73 |
| Mid-tier Leaflet Width Mean (mm) | 96 | 68 |
| Petiole Length Mean (mm) | 215 | 105 |
| Petiole Diameter (mm) | 4 | 4.1 |
| Petiole Color | Yellow-Green 144B (RHS) | 5GY 7/10 (Munsell) |
| Petiolule Length Mean (mm) | 14 | 7.4 |
| Stipule Length Mean (mm) | 25 | 23.3 |
| Stipule Color | Green 143C (RHS) | 5GY 6/8 (Munsell) |
| Serrations per Leaf | 17.74 | 71.8 |
| Number of Leaflets/Leaf | 3 | 3 |
| Leaf Convexity | Most concave | Some flat, most slightly concave |

Detailed foliage characteristics of 'Sweet Eve':

*Leaf.*—Color of adaxial surface — Yellow green (Green 147A). Color of abaxial surface — Light green to nearly gray green (Green 138B). Shape in cross section — Slightly to moderately concave. Blistering — Slight to strong on the mid-tier leaflet. Number of leaflets/leaf — Three.

*Mid-tier leaflet.*—Length/width ratio — Almost as wide as long. Shape — The terminal leaflet is nearly round, slightly wider than long, the two side leaflets are obtuse to oblique. Shape of base — The terminal leaflet base is obtuse. Shape of leaflet apex — The leaflet apex is generally rounded the base of the terminal/mid-tier leaflet is obtuse. Shape of serrations — Slightly pointed to slightly rounded. Venation of leaflets — Pinnate.

*Petiole.*—Pubescence density — Slight. Petiole color — Medium to light green (Yellow-Green 144B).

*Petiolule.*—Mean petiolule diameter — 0.8 cm. Petiolule color — Medium to light green (Yellow-Green 144B).

*Stipule.*—Mean stipule width — 0.5 cm. Stipule color — Medium to dark green (Green 143C). Anthocyanin coloration of stipules — Medium to light pink (Red 56A).

*Attitude of hairs.*—Hairs are perpendicular to the petiole.

*Bract leaflets.*—Length of bract leaflets — 4.3 cm. Width of bract leaflets — 2.9 cm. Shape of bract leaflet — Oval. Shape of bract leaflet apex — Obtuse. Bract leaflet margins — Crenate. Shape of bract leaflet base — Rounded to oblique. Color of adaxial bract leaflet surface — Green to dark green (Green 143A). Color of abaxial bract leaflet surface — Medium green to green (Green 138B). Frequency of bract leaflets — Bract leaflets are present on approximately 80% of flower trusses.

Comparative Flower and Inflorescence Characteristics

Table 6 compares the inflorescence and secondary flower characteristics of 'Sweet Eve' with the inflorescence and secondary flower characteristics of 'Albion'. Inflorescence characteristics are taken from a fully mature plant during full bloom. Flower characteristics are taken from a primary flower at full maturity.

TABLE 6

Quantitative Comparison of 'Sweet Eve' and 'Albion' Inflorescence and Secondary Flower Characteristics

| Characteristic | 'Sweet Eve' | 'Albion' |
|---|---|---|
| Fruiting Truss Length Mean (mm) | 183.8 | 170 |
| Corolla Diameter Mean (mm) | 40 | 27.0 |
| Calyx Diameter Mean (mm) | 36 | 35.8 |
| Petal Length Mean (mm) | 13 | 12.7 |
| Petal Width Mean (mm) | 14.5 | 12.6 |
| Petal Length/Width Ratio | 0.89 | 1.01 |
| Petals per Flower Mean | 5-6 | 5-8 |

Detailed inflorescence characteristics of 'Sweet Eve':

*Position relative to foliage.*—Some internal, mostly even and some exposed.

*Mean fruiting truss diameter.*—0.41 cm.

*Fruiting truss color.*—Medium to dark green (Yellow-Green 144A).

Detailed flower characteristics of 'Sweet Eve':

*Size of calyx relative to corolla.*—Smaller.

*Corolla.*—Size — Medium to large. Mean corolla width — 3.5 cm. Mean corolla depth — 0.8 cm. Petal length to width ratio — Wider than long. Petal shape — Nearly round having an obtuse base and apex, slightly overlapping. Petal margins — Entire. Color of adaxial petal surface — White (White 155C). Color of abaxial petal surface — White (White 155B).

*Calyx.*—Sepal number — 10. Length of sepal — 1.4 cm. Width of sepal — 0.9 cm. Shape of sepal — Elliptic. Shape of sepal apex — Acute to cuspidate. Sepal leaflet margins — Entire. Color of adaxial sepal surface — Green to dark green (Green 137A). Color of abaxial sepal surface — Medium green to green (Yellow-Green 146C).

Pest Reactions

The plants of 'Sweet Eve' exhibit some tolerance to Powdery Mildew (*Podosphaera leucotricha*). The susceptibility of the new cultivar to any of the virus complexes of the United Kingdom has not been determined.

COMPARISON WITH KNOWN VARIETIES

The variety which is believed to be most closely resemble 'Sweet Eve' is 'Albion' (U.S. Plant Pat. No. 16,228). When compared to similar cultivar 'Albion', 'Sweet Eve' differs by the following characteristics.

'Sweet Eve' is a typical day-neutral strawberry cultivar, being stronger in expressing this character than 'Albion' (U.S. Plant Pat. No. 16,228) under United Kingdom growing conditions. The production pattern for 'Sweet Eve', when grown in the United Kingdom, is significantly earlier in the season than that of 'Albion' to reach peak fruiting.

When compared to Albion under United Kingdom growing conditions, 'Sweet Eve' has a fruit shape and uniformity of shape superior to that of 'Albion', a fruit skin significantly firmer but juicier and paler in color than that of 'Albion', an increased numbers of flower trusses and fruit trusses per plant than that of 'Albion', a significantly higher yield than that of 'Albion', and a recurved calyx position relative to the fruit leaving a visible white band at the top of the 'Sweet Eve' fruit.

Further, the fruit of 'Sweet Eve' is significantly better flavored and far sweeter than that of 'Albion' with 'Sweet Eve' having Brix levels averaging 11.1% for fifteen (15) consecutive weeks. Finally, 'Sweet Eve' possesses a refreshing pleasant aroma not found in the 'Albion' cultivar.

'Sweet Eve' plants exhibit a slightly more compact growth habit than that of 'Albion' and when it is grown in the United Kingdom, the plant size is significantly greater than 'Albion'. While 'Sweet Eve' plants are similar in height to 'Albion', 'Sweet Eve' plants produce more crown numbers per plant and a greater volume of leaves than 'Albion.' The leaf size of 'Sweet Eve' is medium, but larger than that of 'Albion', and the leaflets are generally round and almost as wide as long.

The petiole and petiolule lengths of 'Sweet Eve' are greater than that of 'Albion', and the petiole pubescence density of 'Sweet Eve' is significantly less when compared to 'Albion', which has very heavy pubescence. Some hair is present on 'Sweet Eve' at the base of the petiole and close to the stipules. The petiolule pubescence of 'Sweet Eve' is moderate, but still significantly less than that of 'Albion'.

The leaflets of 'Sweet Eve' typically possess a slightly round (obtuse) base and tip; however, the leaflets are not symmetrical. In fact, the leaflets of 'Sweet Eve' express a very distinctive architecture wherein the distance from the petiolule to the first serration is significantly longer on one side compared to the other (approximately 20%). The serrations express a slightly pointed to slightly rounded tips with the leaflets of 'Sweet Eve' plants possessing a significantly smaller number of serrations per leaf than that of 'Albion'. The most outstanding characteristic of the leaves of 'Sweet Eve' are the upwards curving leaflets. Many leaflets of 'Sweet Eve' exhibit slight to strong puckering/blistering, a feature that is visible on both sides particularly on the mid-tier leaflets.

'Sweet Eve' flower trusses tend to grow within the foliage and do not stand out of the leaf canopy. Instead, flowers tend to open at the canopy level, however, when loaded with fruit, the flower trusses tend to protrude to the sides of the plant between the leaves rather than expressing a totally upwards direction. The presence of a bract can be seen on 80% of the flower trusses from early developmental stage, which progresses into a typical leaflet as the truss matures and fruit develops. Generally there are more trusses per plant and more flowers and fruit per truss than that of 'Albion'.

The flowers of 'Sweet Eve' are slightly larger and stronger than those of 'Albion' and generally are greater in number. The primary flowers of 'Sweet Eve' are generally larger than those of 'Albion.' Petal numbers of 'Sweet Eve' are similar to 'Albion', however, the petals of 'Sweet Eve' have an entire margin and the obtuse base and apex and are slightly overlapping. Additionally, 'Sweet Eve' exhibits broader and shorter petals than 'Albion.' The calyx of 'Sweet Eve' is similar to that of 'Albion', however, the calyxes of the primary fruit for 'Sweet Eve' are very simple having one (1) or two (2) indentations. The calyxes on the secondary and tertiary fruit of 'Sweet Eve', however, are completely without any serrations. The calyxes of 'Sweet Eve' are typically recurving causing expression of a white band at the top of the berry.

The berries of 'Sweet Eve' The berries of 'Sweet Eve' are medium to large in size and exhibit a glossy bright orange-red appearance. When grown in the United Kingdom, the fruit of 'Sweet Eve' has a superior shape than that of 'Albion' and is less prone to the ridging exhibited by 'Albion'.

'Sweet Eve' berries are glossier and paler than those of 'Albion.' Specifically, the external and internal fruit color of 'Sweet Eve' is brighter and is substantially lighter than of 'Albion'. During the summer season, the fruit of 'Sweet Eve' retains its bright orange-red color and appears to be unaffected by the higher seasonal temperatures. 'Albion' fruit, however, has a darker skin coloration that typically becomes darker when exposed to higher temperatures. In cooler temperatures, 'Sweet Eve' berries retain their bright orange-red color; however, 'Albion' berry color becomes increasingly darker as the plant transitions from youth to maturity.

The achenes of 'Sweet Eve' berries are characterized as being generally even to slightly indented into the surface of the fruit, however, this indentation is far less dramatic when compared to the achenes of 'Albion.' Sweet Eve' berries generally contain fewer achenes than those of 'Albion'.

'Sweet Eve', significantly sweeter and juicier than 'Albion' throughout the cropping season, provides a very pleasant combination of flavor, sugar, and very low acid levels. The berry skin of 'Sweet Eve' is significantly firmer than that of 'Albion' and does not bruise as readily during rubbing as the latter. 'Sweet Eve' fruit is more aromatic than that of 'Albion' and possesses a very pleasant scent. The fruit flesh of Sweet Eve is less firm than that of 'Albion' providing for a less crunchy texture and a more pleasant eating experience. 'Sweet Eve' retains a very good fruit quality throughout the cropping season and is stable in its essential characteristics, i.e. fruit size, shape, quality, color, firmness, Brix levels, and good plant habit.

Flower initiation and flower expression of 'Sweet Eve' are generally linear; however, variation in the climate might cause slight fluctuation. Termination of flowering is temperature dependent and day-length independent.

Commercial ratings for 'Sweet Eve' are also superior to those of 'Albion' insomuch as the fruits of 'Sweet Eve' have a significantly improved shelf-life, a superior firmness, an outstanding flavor, and a higher level of sugar.

When grown in the United Kingdom under appropriate management, the cropping season for 'Sweet Eve' starts in June, significantly earlier than that of 'Albion', and continues through September. Subject to these growth conditions, 'Sweet Eve' has a more uniform fruit shape and size and produces a substantially greater total yield per plant throughout the cropping season than 'Albion'.

What is claimed is:

1. A new and distinct cultivar of strawberry plant named 'Sweet Eve' substantially as herein described and illustrated by the characteristics set forth above.

* * * * *